United States Patent [19]
Benchetrit

[11] Patent Number: 6,066,777
[45] Date of Patent: May 23, 2000

[54] ANATOMICAL PROSTHESIS FOR THE REPAIR OF HERNIAS BY A LAPAROSCOPIC OR OPEN ROUTE

[75] Inventor: Salomon Benchetrit, Caluire, France

[73] Assignee: Sofradim Production, Trevoux, France

[21] Appl. No.: 08/954,065

[22] Filed: Oct. 20, 1997

[30] Foreign Application Priority Data

Oct. 18, 1996 [FR] France .................................. 96 12932

[51] Int. Cl.[7] .................................................. A61F 2/02
[52] U.S. Cl. .................................................... 623/11
[58] Field of Search ............................ 623/11; 606/151, 606/215, 216

[56] References Cited

U.S. PATENT DOCUMENTS

| | | | |
|---|---|---|---|
| 4,693,720 | 9/1987 | Scharnberg | 623/11 |
| 4,769,038 | 9/1988 | Bendavid et al. | 623/13 |
| 4,878,890 | 11/1989 | Bilweis | 623/11 |
| 5,147,374 | 9/1992 | Fernandez | 606/151 |
| 5,425,740 | 6/1995 | Hutchinson | 606/215 |
| 5,716,408 | 2/1998 | Eldridge | 623/11 |
| 5,716,409 | 2/1998 | Debbas | 623/11 |
| 5,769,864 | 6/1998 | Kugel | 606/151 |

FOREIGN PATENT DOCUMENTS 0 719 527 A1  11/1995  European Pat. Off. .

*Primary Examiner*—Michael J. Milano
*Attorney, Agent, or Firm*—Arent Fox Kintner Plotkin & Kahn PLLC

[57] ABSTRACT

The invention relates to an anatomical prosthesis adapted specially for the inguinal region and intended for the repair of inguinal hernias, especially by a laparoscopic route. It comprises a first and a second plate, each comprising a porous and flexible prosthetic material, and these being connected to one another along a connection line by a connection means. The two plates are asymmetrical in relation to one another, and, in a deployed configuration of the prosthesis, the second plate has at least one undulated developed shape, and anatomical so as to match the general shape of the lower inguinal structures, and correspondingly the connection line has at least one undulated curved shape, the generatrix describing this developed shape and passing through the connection line being directed at an aperture angle θ at most equal to 150° relative to the plane of the first plate.

17 Claims, 4 Drawing Sheets

ANATOMICAL PROSTHESIS FOR THE REPAIR OF HERNIAS BY A LAPAROSCOPIC OR OPEN ROUTE

BACKGROUND OF THE INVENTION

1. Field of the Invention

The present invention relates to an anatomical prosthesis for the repair of hernias, and in particular a prosthesis adapted for the repair of inguinal hernias by laparoscopy.

2. Description of the Related Art

In a general manner, prostheses for the repair of the inguinal region and for the treatment of hernias are well known, and consist in particular of one or more porous prosthetic plates, made of a biocompatible synthetic material, which may or may not be absorbable, for example polyethylene, polypropylene, polyester, or similar, optionally having undergone a surface treatment to render it biocompatible with the cellular medium in which they are implanted.

These prostheses can be obtained, for example, by joining together two plates of prosthetic material by knitting. Such a prosthesis has been described in the American patent U.S. Pat. No. 4,769,038, granted to Bendavid et al., this prosthesis being designed essentially for the complete reconstruction of the inguinal region. In accordance with this patent, the prosthesis comprises a first plate, being a substantially plane upper plate, and a second plate, being a lower plate, the plates each comprising a porous and flexible prosthetic material. These plates of generally elongate shape are connected to one another along a straight connection line by a connection means, for example a seam. The prosthesis additionally comprises a third plate which is connected to the two others along the same straight connection line, and by the same seam.

When repair of a hernia in the inguinal region is being performed by a posterior and extraperitoneal laparoscopic route, it is very important to be able to locate, and to cover with the prosthesis, certain anatomical elements of the anterior wall of the abdomen, which elements may be described as follows, from the inside outwards, and for the right-hand side of the body:

- to the inside, the anterior retro-parietal space is limited towards the front by the rectus abdominis muscles, towards the rear by the peritoneum, and underneath by the upper edge of the os pubis;
- the middle part is limited towards the front by the fascia transversalis, and the conjoint tendon, with the iliac vessels below, and with the transverse muscle above;
- in the outer part, towards the front there is the internal orifice of the inguinal canal with the elements of the spermatic cord (spermatic vessels and ductus deferens), with the psoas muscle below, and with the transverse muscle above.

In summary, and this constitutes the starting point of the present invention, it is noted that the inguinal region is particular in that the elements described hereinabove are not all in the same spatial plane, but are disposed in an oblique arrangement from the top downwards, and from the outside inwards. In the case of an inguinal hernia, the prosthesis implanted after reduction of the hernia must ensure satisfactory covering by adapting to the contours of the region and by respecting the obliqueness of the inguinal space, if possible without leaving any empty spaces.

This requirement poses a considerable problem when using the known prostheses, since none of these is really adapted to the anatomy of the site of the surgical intervention, a fact which compels the surgeon to cut the prosthesis, often several times, in order to obtain a prosthesis which is more or less well suited. Now, a poor covering of the anatomical elements described hereinabove is probably one of the main causes of recurrence of hernias, and such hernias may be even more difficult to treat because of the deterioration of the anatomical structures which has been provoked by the earlier hernia.

BRIEF SUMMARY OF THE INVENTION

Therefore, the subject of the present invention is an anatomical prosthesis which does not require any substantial cutting beforehand, and more particularly intended for the repair of inguinal hernias by a posterior and extraperitoneal laparoscopic route, ensuring good covering of the inguinal space, without, in order to do this, preforming (for example by thermo-forming) the flexible material from which each plate is made.

The prosthesis according to the invention differs from the known prostheses in that it includes two plates which are asymmetrical in relation to one another, and, in the deployed configuration of the prosthesis, the second plate has at least one undulated developed and anatomical shape so as to match the general shape of the lower inguinal structures, especially the spermatic and iliac vessels, and the psoas muscle, and correspondingly the connection line has at least one undulated curved shape, the generatrix describing the said developed shape and passing through the connection line being directed at an aperture angle θ, equal at most to 150° relative to the plane of the first plate.

A prosthesis such as is defined above ensures covering of all the anatomical elements described above, without leaving empty spaces which are likely to be the cause of a recurrence. In particular, the region around the iliac and spermatic vessels is particularly well protected.

Furthermore, this prosthesis offers increased comfort for the subject in whom it is implanted, since unlike the known prostheses it requires few if any fixing staples. The prosthesis according to the present invention remains in place by itself, because the connection line is positioned at the intersection of the parietal and vascular planes. This allows the prosthesis to follow the changes in the relative position of the different anatomical elements of the inguinal region, which changes result from the normal movement of the abdominal muscles of the subject, without however shifting outside the region of implantation. By comparison, the prostheses which are known, and such as are described in the aforementioned American patent, are stapled or fixed by sutures to the surrounding abdominal structures, and thus tensioned, and a quite commonplace muscle movement, for example the act of coughing, or getting up from a seated position, often provokes an unpleasant sensation, or even pain.

Furthermore, a prosthesis according to the invention can be easily introduced and implanted in the inguinal space using the usual laparoscopic or open techniques. The connection line, incorporating the connection means (seam, for example), both flexible in its length, but relatively rigid, acts like a beam, setting the axis of positioning of the prosthesis, while at the same time acting as a hinge for its deployment.

According to one preferred embodiment of the prosthesis of the present invention, the second plate has two developed undulated shapes, a first developed undulated shape matching the shape of the psoas muscle, and a second developed undulated shape matching the shape of the iliac and spermatic vessels.

In one preferred embodiment, the first and second plates are each made of the same prosthetic material. However, it has proven advantageous for the first and second plates each to be made of a different prosthetic material exhibiting different flexibility. It has in fact been found to be particularly advantageous, for example, for the first plate to be made of a relatively rigid prosthetic material, for example a knitted fabric or woven fabric of single thickness, and for the second plate to be made of a relatively flexible prosthetic material, for example a knitted fabric or a woven fabric of double thickness. In this way, the first plate, being the upper plate, of the prosthesis can stand "upright" as it were, in a substantially vertical manner, remaining, by means of the connection line, on the line of intersection of the parietal and vascular planes.

According to one preferred embodiment, the first plate has, in the deployed configuration of the prosthesis, a substantially L-shaped form tilted over to the right, defining an upper part of greater surface area, and a lower part, on the left-hand side, of smaller surface area. of course, the first plate can have, again in a preferred manner, in the deployed configuration of the prosthesis, a shape which is the mirror image of the above-described substantially L-shaped form tilted over to the right, defining an upper part of greater surface area, and a lower part, on the right-hand side, of smaller surface area.

Furthermore, the first plate can also have at least one undulation along a transverse edge and along the connection line and complementary to the undulation of the second plate.

The connection means, for example a mobile seam, allows the two plates to move in a limited manner in relation to one another in order to adjust to the changes in the relative position of the anatomical elements of the inguinal region. The connection means is advantageously obtained by overstitching a transverse edge of each plate.

Thus, the aperture angle θ between the first plate and the second plate is variable, depending on the relative position of the said anatomical elements, and is at most equal to 150°.

According to one preferred embodiment, the first plate is slotted from an outer edge thereof up to a position near the connection means.

Furthermore, and advantageously, at least one of the first and second plates can have a cutout adapted to surround the spermatic cord. In one embodiment according to the present invention, both plates have a cutout adapted to surround the spermatic cord.

Still more preferably, the first plate is slotted and has a front leaf equipped with an edge extending, substantially perpendicular to the connection line, from an outer edge of the first plate towards a cutout, and a rear leaf equipped with an edge extending, substantially oblique to the connection line, from an outer edge of the first plate towards the cutout, the front leaf thereby at least partially covering the rear leaf.

Finally, and preferably, at least one of the first and second plates includes means for ordered and structured folding of the plate or plates, for example one or more filaments interlaced in the meshes. The advantage of this is that it allows the surgeon to reduce the size of the plate or plates in an ordered manner, by simply pulling on the filaments, so as to be able to insert the prosthesis in a trocar, and then to deploy it once again inside the body, again in an ordered manner.

In a variant of the invention, the anatomical prosthesis is a bilateral prosthesis, formed by a continuation of the first plate along its transverse edges, and a third plate, the shapes and arrangement of the continuation and of the third plate being substantially a mirror image of the first plate and of the second plate, respectively, about an axis of symmetry in the same plane as the said first plate.

In accordance with all these characteristics, a completely anatomical prosthesis is obtained, to the point of being able to distinguish and manufacture left-side and right-side prostheses according to the invention. This prosthesis is obtained starting from all suitable materials, as long as they are sufficiently porous to be colonized by the surrounding cells, and to some extent integrated, and biocompatible with the tissues and media of the inguinal space, and mechanically resistant, especially to traction, the connection means being at least as mechanically resistant as the weaker of the two plates. Preference will be given to a cloth (woven fabric or knitted fabric), or a nonwoven, obtained from natural or synthetic fibres or filaments, for example polypropylene or polyester.

BRIEF DESCRIPTION OF THE SEVERAL VIEWS OF THE DRAWINGS

The present invention will be better understood from the following detailed description and drawing which are given by way of nonlimiting example, and in which drawing.

DETAILED DESCRIPTION OF THE INVENTION

Figure 1:
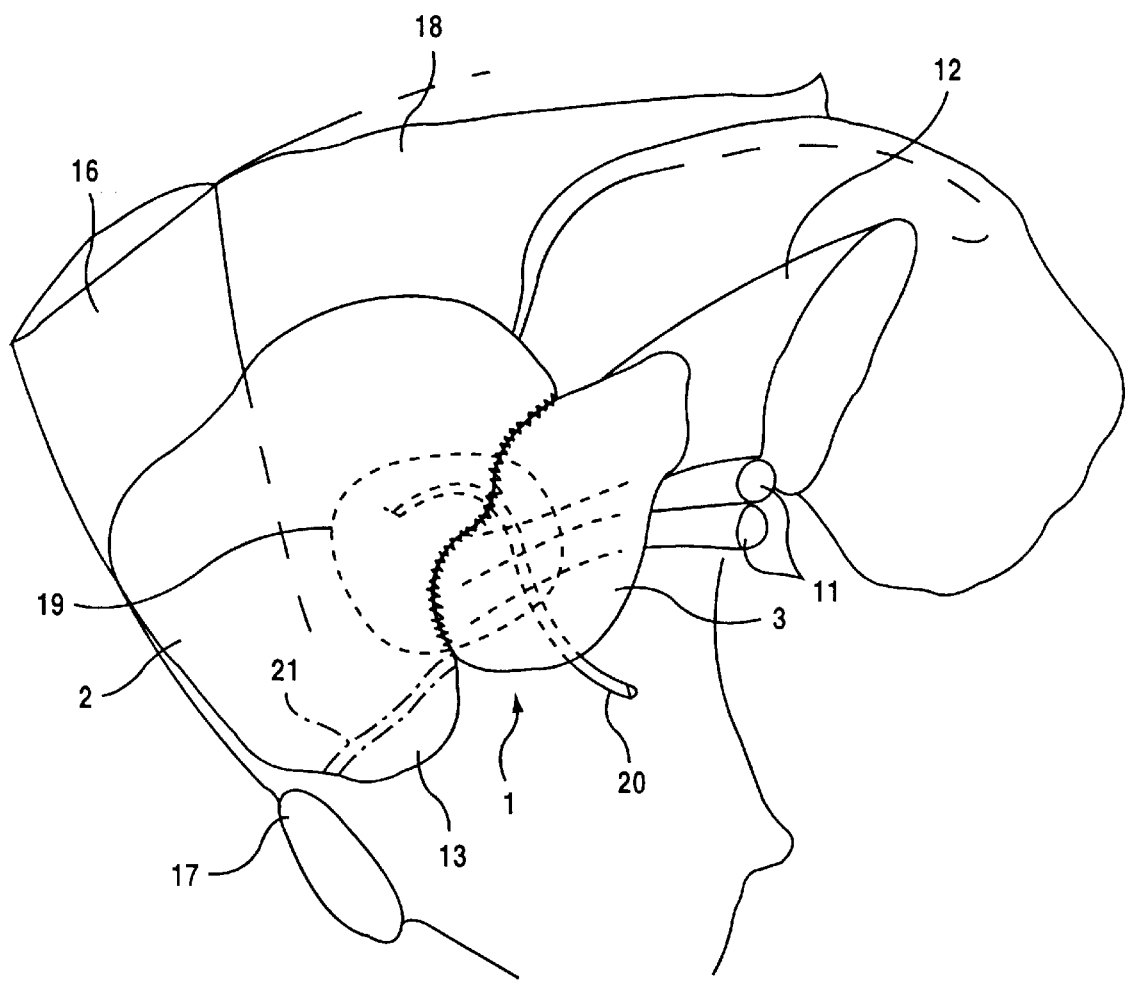
FIG. 1 represents a perspective view of the positioning of the prosthesis according to the present invention in relation to the anatomical elements of the extraperitoneal inguinal region, on the right-hand side of a human body, as seen from the inside outwards, that is to say towards the outside of the body.

In accordance with the figures, and in particular FIG. 1, the prosthesis according to the present invention is used for repairing inguinal hernias by a posterior laparoscopic or open route. The technique employed in the laparoscopic intervention, for example, is well known to the skilled expert and will, therefore, not be described in detail. In brief, one or more trocars are introduced into the extraperitoneal space, that is to say posterior to the rectus abdominis muscle and the fascia transversalis, the extraperitoneal operating space being created by insufflation and separation of the peritoneum and the abdominal wall. The perspective view shown in FIG. 1 thus represents a view of the positioning of the prosthesis according to the present invention in relation to the anatomical elements of the extra-peritoneal inguinal region, on the right-hand side of a human body, as viewed from the inside outwards, that is to say towards the outside of the body. The following anatomical elements of the anterior wall of the abdomen can be seen, from the inside outwards, and for this right-hand side of the body:

to the inside, the anterior retro-parietal space is limited towards the front by the rectus abdominis muscle 16, towards the rear by the peritoneum (not shown), and underneath by the upper edge of the os pubis 17;

the middle part is limited towards the front by the fascia transversalis (not shown), and the conjoint tendon, with the iliac vessels 11 below, and with the transverse muscle 18 above;

in the outer part, towards the front there is the internal orifice 19 of the inguinal canal with the elements of the spermatic cord (spermatic vessels), with the psoas muscle 12 below, and with the transverse muscle 18 above.

In this figure it can be clearly seen that the inguinal region is particular in that the elements described hereinabove are not all in the same spatial plane, but are disposed in an oblique arrangement from the top downwards, and from the outside inwards. In the case of an inguinal hernia, the prosthesis implanted after reduction of the hernia must ensure satisfactory covering by adapting to the contours of the region and by respecting the obliqueness of the inguinal space. FIG. 1 also shows the positioning of the prosthesis, and its general shape, the details of which are given hereinafter.

Figure 2:
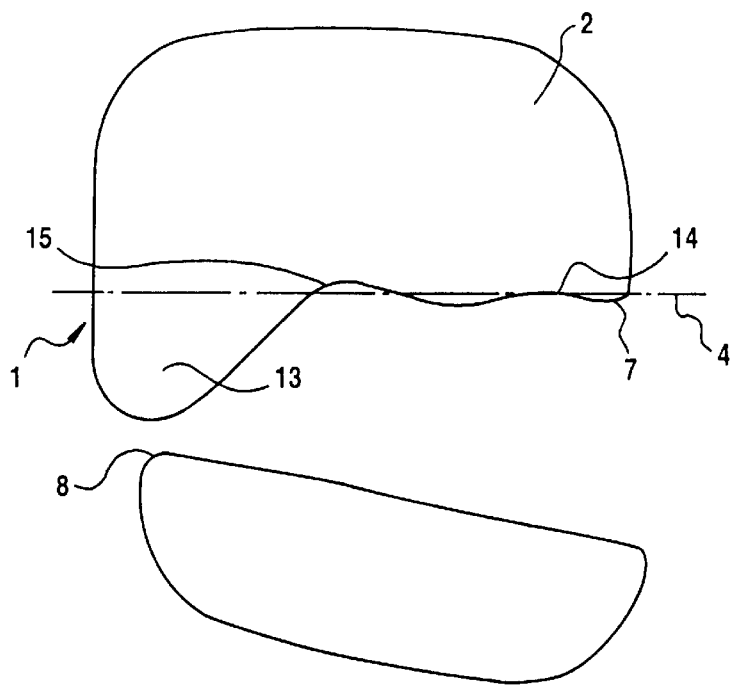
FIG. 2 represents a plan view of the general shapes of a first plate and of a second plate constituting the anatomical prosthesis according to the present invention.
Figure 3:
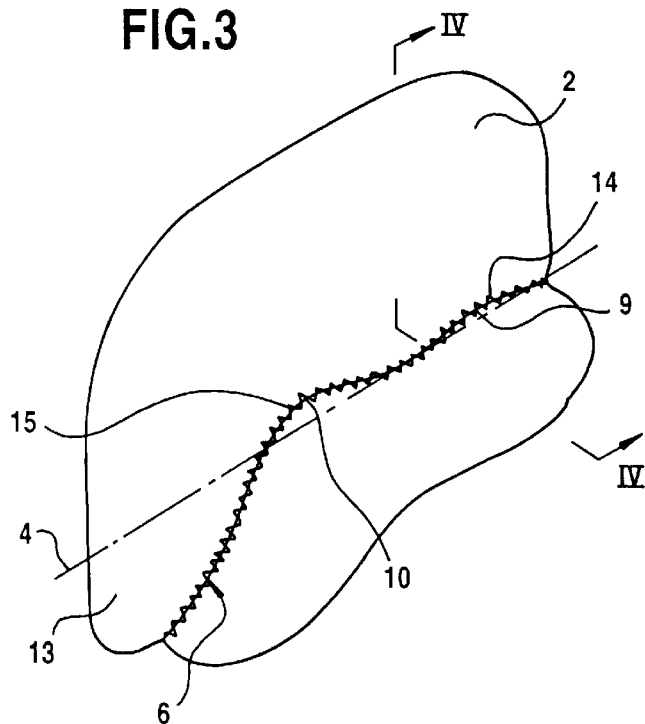
FIG. 3 represents a perspective view of the two plates of the prosthesis according to the invention, which are connected to one another by a mobile seam, and illustrating more clearly the anatomical shapes of each plate.
Figure 4:
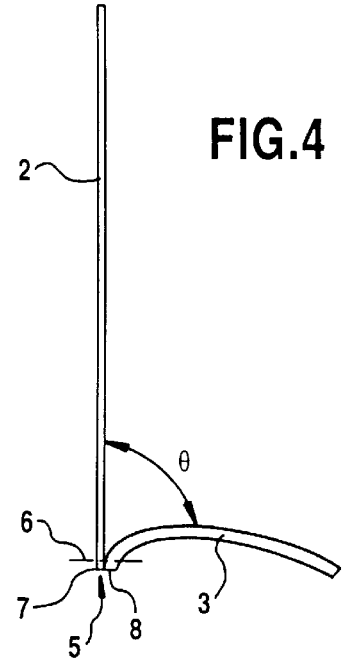
FIG. 4 represents a transverse section through the prosthesis according to the invention along the line IV—IV in FIG. 3.

In a preferred embodiment, and such as is represented in FIGS. 2 to 4, the prosthesis 1 according to the invention comprises a first plate 2, which is substantially a plane, and a second plate 3, the two plates each comprising a porous and flexible prosthetic material, optionally coated with an agent promoting cell colonization, or preventing such cell colonization. It is important to note that the two plates are asymmetrical in relation to one another, which means that depending on which side the hernia to be treated is situated, a left-side prosthesis or a right-side prosthesis will be used. The prosthetic material of the first plate may be different, and/or exhibit different mechanical properties, from the material of the second plate, and for this reason the two plates can exhibit different flexibility.

In the preferred embodiment, the first plate 2 is made of a relatively rigid prosthetic material, for example a knitted fabric or a woven fabric of single thickness, and the second plate 3 is made of a relatively flexible prosthetic material, for example a knitted fabric or a woven fabric of double thickness, preferably of the order of 1.5 mm to 2 mm. The two plates are generally made of any biocompatible material, which may or may not be absorbable, and preferably of a textile material based on multifilament polyester yarn. A prosthesis constructed in this way makes it possible, at one and the same time, to give the prosthesis a certain rigidity, facilitating its handling and implantation by the surgeon, as well as a flexibility allowing it to match all the anatomical shapes in the inguinal region. Furthermore, a prosthesis formed in this way tends to "sit", as it were, at the bottom of the inguinal region without being displaced, which was a recognized problem of the traditional prosthetic plates for repairing inguinal hernias, and the first plate holds itself substantially "upright". Preferably, the first plate 2 can have a height of up to about 15 cm, and the second plate 3 can have a depth of between about 2 cm and about 6 cm. In addition, the plates may be optionally covered with a biological substance, for example collagen, in particular bovine type I collagen, or else with a biocompatible polymer substance.

The plates 2, 3 are connected to one another along a connection line 4 by a connection means, indicated generally by the reference number 5. In the embodiment shown in the figures, for example FIGS. 3 and 4, but in a nonlimiting manner, this connection means is a mobile seam 6. FIG. 4, which is a cross-sectional view of FIG. 3 along lines IV—IV, shows the two plates 2, 3 connected to one another by such a seam, as well as the transverse edges 7, 8 of each plate. This seam is advantageously obtained by overstitching the plates 2, 3 along and in proximity to a transverse edge 7, 8 of each plate (cf. FIG. 2). The mobile seam 6 permits a relative displacement of the first 2 and second 3 plates in relation to one another, which increases the capacity of the plate to adapt to the muscle movements of the person in whom it is implanted. It must be appreciated that the connection means 5 is not limited to such a seam 6, and that other connections are possible, for example by stapling, knitting, welding or adhesive bonding of the two plates, as long as the prosthesis remains anatomical and can match the anatomical shapes of the inguinal structures without leaving any noticeable space.

In the deployed configuration of the prosthesis 1, that is to say when it is implanted in the body, the second plate 3 has at least one undulated developed and anatomical shape, so as to match the general shape of the lower inguinal structures, namely the spermatic and iliac vessels 11, and the psoas muscle 12. According to the preferred embodiment illustrated in FIG. 3, the first plate 2 includes two undulations 14, 15, a first undulation 14 matching the shape of the psoas muscle 12, and a second undulation 15 matching the shape of the iliac and spermatic vessels 11.

In this case, complementing the undulated developed shapes 9, 10 of the second plate 3.

In accordance with FIG. 2, the connection line 4 also has two undulated curves corresponding to the undulated developed shapes of the second plate 3. A generatrix describes the undulated developed shapes 9, 10 and passes through the connection line 4 and is directed at an aperture angle at most equal to 150° relative to the plane of the first plate 2.

As can be seen in FIGS. 2 to 4, and for a prosthesis for repair of a right-side hernia, the first plate 2 advantageously has a substantially L-shaped form tilted over to the right, thus defining an upper part of greater surface area, and a lower part 13, on the left-hand side, of smaller surface area. For a left-side prosthesis, the mirror image of that illustrated in FIGS. 2 to 4 will be taken, for example.

When the prosthesis has been implanted (reference may usefully be made to FIG. 1), the part of greater surface area of the first plate 2 rests on the anterior muscle wall (especially the rectus abdominis 16 and transverse muscle 18). The part 13 of smaller surface area of the first plate 2 will cover the upper end of the pubis and the pectineal ligament 21 (represented in dot-and-dash lines). The undulations 9, 10 of the second plate 3 match the iliac and spermatic vessels 11 and the psoas muscle 12 substantially completely, and without leaving any appreciable spaces, and the transverse edges 7, 8 rest on the line of intersection of the parietal and vascular planes. The ductus deferens 20 is also covered, which is not the case with the prostheses of the prior art which are often equipped with slots or holes in one of the plates in order to permit the passage of this duct and to act as a "stirrup" for the latter, in order to prevent recurrence of indirect inguinal hernias.

Figure 5:
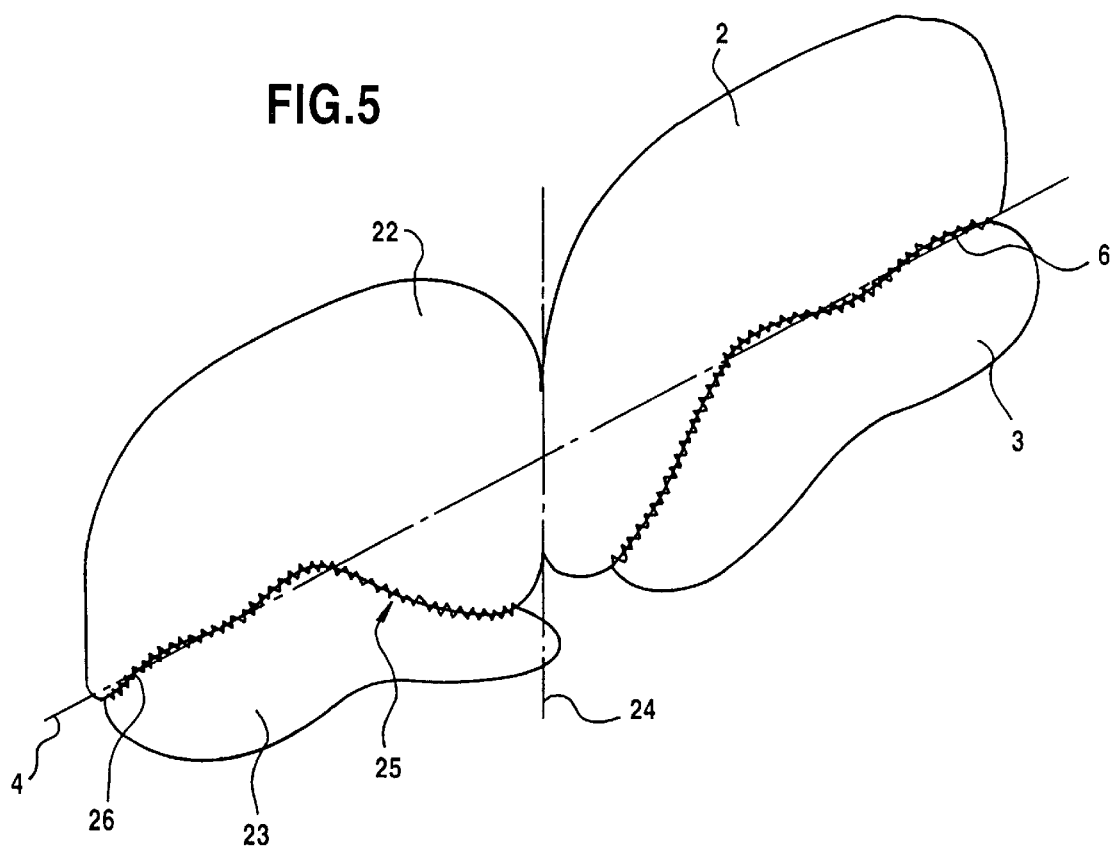
FIG. 5 represents a variant of the prosthesis according to the invention, for repair of a bilateral hernia.

In a variant of the present invention, and as is illustrated in FIG. 5, the prosthesis is a bilateral prosthesis, serving to repair a bilateral hernia. Thus, the prosthesis assumes the shape of a right-side and left-side prosthesis, such as they have been described above, joined together or manufactured in a continuous or noncontinuous manner. The first plate 2 thus has a continuation 22 along its transverse edges, and the prosthesis includes a third plate 23, with respect to the definition already given thereof, and the shapes and arrangement of the continuation 22 and of the third plate 23 are substantially a mirror image of the first plate 2 and of the second plate 3, respectively, about an axis of symmetry 24 in the same plane as the said first plate 2. The third plate is connected to the first plate by the connection means 25, which assumes the form of a mobile seam 26 in this embodiment of the invention, and as is illustrated in FIG. 5. This prosthesis can be positioned substantially in the same way as in the case of the preferred embodiment already discussed.

Figure 6:
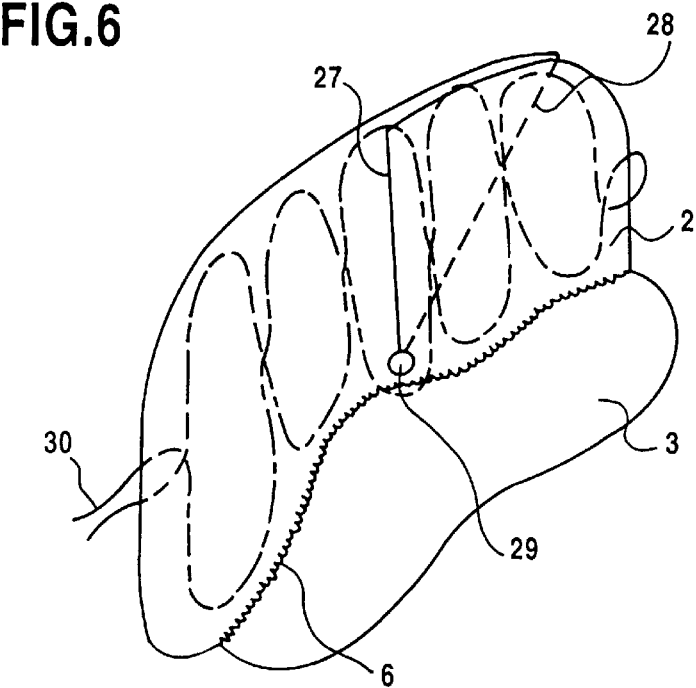
FIG. 6 represents another preferred embodiment of the basic anatomical prosthesis illustrated in FIG. 1, with slight modifications.
Figure 7:
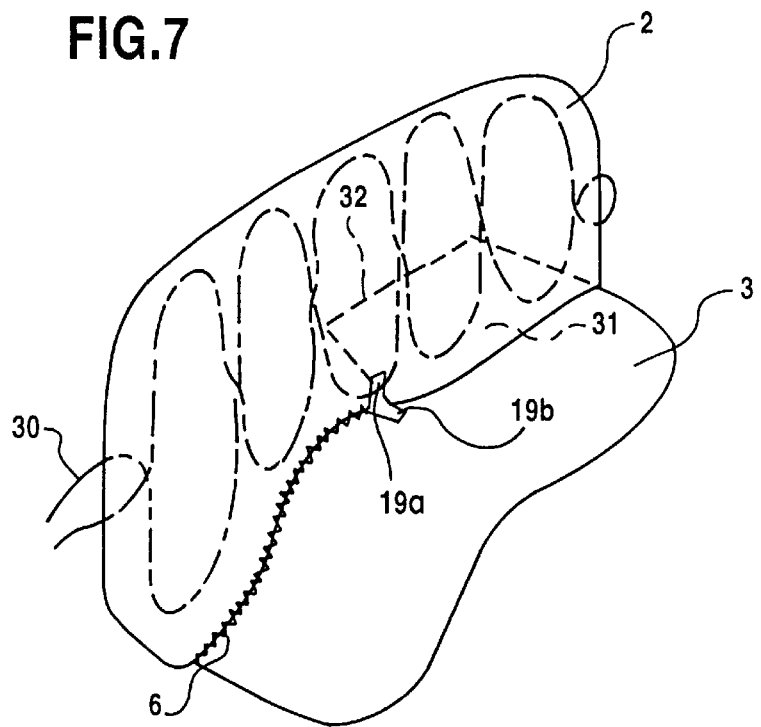
FIG. 7 represents yet another embodiment of the basic anatomical prosthesis illustrated in FIG. 1.

FIGS. 6 and 7 represent other preferred embodiments of the basic anatomical prosthesis as it has been illustrated in FIGS. 1 to 4. According to FIG. 6, the first plate 2 of the prosthesis is equipped with a cutout adapted to surround the spermatic cord 11 and is slotted to form two leaves 27, 28. A front leaf 27 has an edge extending, substantially perpendicular to the connection line 4, from the outer edge of the first plate 2 towards the cutout 29, and a rear leaf 28 has an edge extending, substantially oblique (indicated in broken lines) to the connection line 4, from the outer edge of the first plate 2 towards the said cutout 29, the front leaf 27 thereby at least partially covering the rear leaf 28. This structure makes it possible to introduce the prosthesis and arrange it around the spermatic vessels, while at the same time affording a sufficient covering of the anterior abdominal region, and additionally makes it possible to dispense with closing the slot by suturing or stapling. The prosthesis illustrated in FIG. 6 also has means 30 for ordered folding of the prosthesis, allowing the latter to be gathered together in a structured manner in order to facilitate its introduction into a trocar, as well as its deployment inside the body. These folding means can be, for example, surgical filaments interlaced between the meshes of the plate or plates of the prosthesis.

The prosthesis illustrated in FIG. 7 will be described only in terms of the ways in which it differs from that in FIG. 6. Thus, the first plate 2 is not slotted, and instead a substantially horizontal slot is created between the two plates by virtue of the fact that they are connected to one another only over part of their transverse edges. In addition, each plate 2, 3 includes a cutout 29a, 29b adapted to surround the spermatic cord, and the second plate 3 has a continuation 31 with a substantially straight edge. In the deployed position of the prosthesis, this continuation 31 in fact passes underneath the lower edge of the first plate 2, and is folded back behind the latter by the abdominal wall in such a way as to form an acute angle with the rest of the second plate.

The advantages of the prosthesis according to the present invention are many, since the adaptation of its shape to the retroperitoneal anatomy of the inguinal region facilitates its positioning and consequently reduces the time needed to implant it. Moreover, when the material constituting the second plate is flexible, for example three-dimensional woven fabric, this flexibility, together with the porosity of the material, facilitates the moulding of the prosthesis to the abdominal contours.

These advantages have been demonstrated in a clinical follow-up study of human patients with an unslotted prosthesis according to the invention in two independent centres, with the following results:

Number of hernias treated:
  252 with fixed prostheses (one attachment on the pectineal ligament and one attachment on the abdominal wall);
  51 with unfixed prostheses.
Approach used:
  Extraperitoneal laparoscopy.
Average recovery time:
  Six months for the group with fixed prostheses;
  Four months for the group with unfixed prostheses.
Minimum/maximum duration of follow-up:
  One month/twelve months.
Results:
  Early migration (total for both groups): 0
  Recurrences: 0
  Sepsis: 0
  Complications attributable to shape of prosthesis: 0.

What is claimed is:

1. An anatomical prosthesis adapted specially for the inguinal region and intended for the repair of inguinal hernias by a posterior laparoscopic or open route, the prosthesis comprising a first plate, which is substantially planar, and a second plate, the said plates each comprising a porous and flexible prosthetic material, and being connected to one another along a connection line by a connector, the two plates being asymmetrical in relation to one another, and, in the deployed configuration of the prosthesis, the second plate having at least one undulated developed and anatomical shape so as to match the general shape of the lower inguinal structures, and correspondingly the connection line having at least one undulated curved shape, the generatrix describing the said developed shape and passing through the connection line being directed at an aperture angle $\theta$, equal at most to 150°, relative to the plane of the first plate.

2. The anatomical prosthesis according to claim 1, wherein the second plate has two developed undulated shapes, a first developed undulated shape matching the shape of the psoas muscle, and a second developed undulated shape matching the shape of the iliac and spermatic vessels.

3. The anatomical prosthesis according to claim 1, wherein the first and second plates are each made of the same prosthetic material.

4. The anatomical prosthesis according to claim 1, wherein the first and second plates are each made of a prosthetic material exhibiting a different flexibility.

5. The anatomical prosthesis according to claim 1, wherein the first plate is made of a prosthetic material, which is more rigid than the prosthetic material of the second plate.

6. The anatomical prosthesis according to claim 1, wherein the first plate has, in the deployed configuration of the prosthesis, a substantially L-shaped form tilted over to the right, defining an upper part of greater surface area, and a lower part, on the left-hand side, of smaller surface area.

7. The anatomical prosthesis according to claim 1, wherein the first plate has, in the deployed configuration of the prosthesis, a shape which is the mirror image of a substantially L-shaped form tilted over to the right, defining an upper part of greater surface area, and a lower part, on the right-hand side, of smaller surface area.

8. The anatomical prosthesis according to claim 1, wherein the connector is obtained by overstitching a transverse edge of each plate.

9. The anatomical prosthesis according to claim 1, wherein said prosthesis is a bilateral anatomical prosthesis formed by a continuation of the first plate along its transverse edges, and a third plate, the shapes and arrangement of the continuation and of the third plate being substantially a mirror image of the first plate and of the second plate, respectively, about an axis of symmetry in the same plane as the first plate.

10. The anatomical prosthesis according to claim 1, wherein the first plate is slotted from an outer edge thereof up to a position near the connector.

11. The anatomical prosthesis according to claim 1, wherein at least one of the first and second plates has a cutout adapted to surround the spermatic cord.

12. The anatomical prosthesis according to claim 11, wherein both plates have a cutout adapted to surround the spermatic cord.

13. The anatomical prosthesis according to claim 1, wherein the first plate is slotted and has a front leaf provided with an edge extending substantially perpendicular to the connection line from an outer edge of the first plate towards a cutout and a rear leaf provided with an edge extending substantially oblique to the connection line from an outer edge of the first plate towards the cutout, the front leaf thereby at least partially covering the rear leaf.

14. The anatomical prosthesis according to claim 1, wherein at least one of the first and second plates includes means for ordered and structured folding of the plate or plates.

15. The anatomical prosthesis according to claim 1, wherein said connector is a seam.

16. The anatomical prosthesis according to claim 1, wherein the undulated developed and anatomical shape is configured to match the general shape of the spermatic and iiliac vessels and the psoas muscle.

17. The anatomical prosthesis according to claim 14, wherein said means for ordered and structured folding of the plate or plates comprises one or more filaments interlaced in mesh forming said prosthetic material.

* * * * *